United States Patent
Pilz et al.

(10) Patent No.: US 9,968,536 B2
(45) Date of Patent: *May 15, 2018

(54) COMPOSITION COMPRISING ISOSORBIDE MONOESTERS AND ISOSORBIDE DIESTERS

(71) Applicant: Clariant International Ltd., Muttenz (CH)

(72) Inventors: Maurice Frederic Pilz, München (DE); Peter Klug, Grossostheim (DE); Franz-Xaver Scherl, Burgkirchen (DE); Joerg Grohmann, Niedernhausen (DE)

(73) Assignee: Clariant International Ltd., Muttenz (CH)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/240,813

(22) Filed: Aug. 18, 2016

(65) Prior Publication Data

US 2016/0354296 A1 Dec. 8, 2016

Related U.S. Application Data

(62) Division of application No. 14/237,071, filed as application No. PCT/EP2012/003250 on Jul. 31, 2012, now Pat. No. 9,445,595.

(30) Foreign Application Priority Data

Aug. 4, 2011 (DE) .......................... 10 2011 109 498

(51) Int. Cl.

| | |
|---|---|
| A61K 8/49 | (2006.01) |
| A01N 43/90 | (2006.01) |
| A01N 25/04 | (2006.01) |
| C11D 1/66 | (2006.01) |
| C11D 3/20 | (2006.01) |
| C11D 3/22 | (2006.01) |
| A61Q 19/00 | (2006.01) |

(Continued)

(52) U.S. Cl.
CPC ............ *A61K 8/4973* (2013.01); *A01N 25/04* (2013.01); *A01N 43/90* (2013.01); *A61Q 19/00* (2013.01); *A61Q 19/007* (2013.01); *C09D 7/1216* (2013.01); *C09D 7/1233* (2013.01); *C11D 1/143* (2013.01); *C11D 1/667* (2013.01); *C11D 1/75* (2013.01); *C11D 1/83* (2013.01); *C11D 3/2096* (2013.01); *C11D 3/221* (2013.01); *C11D 3/48* (2013.01); *A61K 2800/10* (2013.01); *A61K 2800/48* (2013.01); *A61K 2800/524* (2013.01)

(58) Field of Classification Search
CPC ............................. A61K 8/4973; A01N 43/90
See application file for complete search history.

(56) References Cited

U.S. PATENT DOCUMENTS

| | | |
|---|---|---|
| 3,331,742 A | 7/1967 | Babayan |
| 4,637,930 A | 1/1987 | Konno et al. |
| (Continued) | | |

FOREIGN PATENT DOCUMENTS

| | | |
|---|---|---|
| CA | 1231046 | 1/1988 |
| DE | 3328372 | 3/1984 |
| (Continued) | | |

OTHER PUBLICATIONS

U.S. Appl. No. 13/321,199, filed Jan. 3, 2012, now published as US2012-0100085.

(Continued)

*Primary Examiner* — Golam M Shameem
(74) *Attorney, Agent, or Firm* — Tod A. Waldrop

(57) ABSTRACT

What are described are compositions comprising one or more compounds of the formula (I) and one or more compounds of the formula (II)

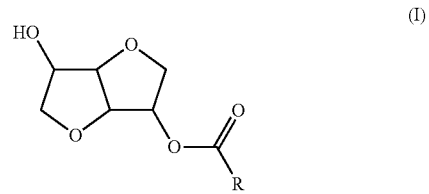

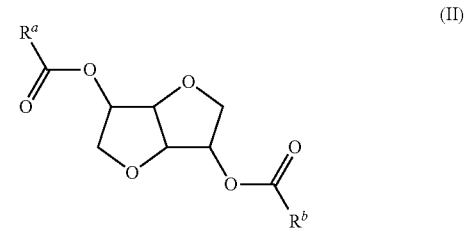

in which

R, $R^a$ and $R^b$ each independently of one another are straight-chain or branched saturated alkyl groups having 5 to 11 carbon atoms or straight-chain or branched mono- or polyunsaturated alkenyl groups having 5 to 11 carbon atoms, wherein the total amount of the compounds of the formulae (I) and (II), based on the total weight of the compositions, is at least 60% by weight.

In an advantageous manner, the compositions are suitable for producing cosmetic, dermatological or pharmaceutical compositions, crop protection formulations, washing or cleaning compositions or paints or coatings.

9 Claims, No Drawings

(51) Int. Cl.
  *C09D 7/12* (2006.01)
  *C11D 1/14* (2006.01)
  *C11D 1/75* (2006.01)
  *C11D 1/83* (2006.01)
  *C11D 3/48* (2006.01)

(56) References Cited

U.S. PATENT DOCUMENTS

| | | | |
|---|---|---|---|
| 4,711,775 | A | 12/1987 | Dittmar et al. |
| 4,847,088 | A | 7/1989 | Blank |
| 6,413,529 | B1 | 7/2002 | Beerse et al. |
| 9,295,626 | B2 * | 3/2016 | Pilz .................. A01N 43/90 |
| 9,358,199 | B2 * | 6/2016 | Pilz .................. C09D 7/002 |
| 9,445,595 | B2 * | 9/2016 | Pilz .................. C11D 1/667 |
| 2005/0222276 | A1 | 10/2005 | Schmaus et al. |
| 2007/0178144 | A1 | 8/2007 | Hameyer et al. |
| 2008/0142023 | A1 | 6/2008 | Schmid |
| 2008/0312195 | A1 | 12/2008 | Simsch et al. |
| 2010/0113664 | A1 | 5/2010 | Bradshaw et al. |
| 2011/0104085 | A1 | 5/2011 | Klug et al. |
| 2011/0117036 | A1 | 5/2011 | Chaudhuri et al. |
| 2012/0015893 | A1 | 1/2012 | Herrwerth et al. |
| 2012/0035090 | A1 | 2/2012 | Breffa et al. |
| 2012/0100085 | A1 | 4/2012 | Klug et al. |
| 2012/0101135 | A1 | 4/2012 | Klug et al. |
| 2012/0116101 | A1 | 5/2012 | Fuertes et al. |
| 2014/0308224 | A1 | 10/2014 | Pilz et al. |
| 2014/0315996 | A1 | 10/2014 | Pilz et al. |
| 2014/0322151 | A1 | 10/2014 | Pilz et al. |
| 2014/0323592 | A1 | 10/2014 | Pilz et al. |
| 2014/0329870 | A1 | 11/2014 | Pilz et al. |
| 2014/0343171 | A1 | 11/2014 | Pilz et al. |
| 2014/0348763 | A1 | 11/2014 | Pilz et al. |
| 2014/0369943 | A1 | 12/2014 | Pilz et al. |
| 2015/0030553 | A1 | 1/2015 | Pilz et al. |
| 2016/0000080 | A1 | 1/2016 | Pilz et al. |

FOREIGN PATENT DOCUMENTS

| | | |
|---|---|---|
| DE | 2234009 | 12/1987 |
| EP | 1813251 | 8/2007 |
| EP | 1972330 | 9/2008 |
| EP | 2239315 | 10/2010 |
| JP | 59-175408 | 10/1984 |
| JP | H 01313408 | 12/1989 |
| JP | H 03168075 | 7/1991 |
| JP | H 08173787 | 7/1996 |
| JP | H 08187070 | 7/1996 |
| JP | H 09291016 | 11/1997 |
| JP | 2002541181 | 12/2002 |
| JP | 2003238396 | 8/2003 |
| JP | 2007203288 | 8/2007 |
| JP | 2008094755 | 4/2008 |
| JP | 2009078984 | 4/2009 |
| WO | WO 2006103338 | 10/2006 |
| WO | WO 2008119841 | 10/2008 |
| WO | WO 2008155159 | 12/2008 |
| WO | WO 2010108738 | 9/2010 |

OTHER PUBLICATIONS

U.S. Appl. No. 14/237,024, filed Jul. 16, 2014, now published as US 2014-0343171.
U.S. Appl. No. 14/237,039, filed Jul. 9, 2014, now published as US 2014-0315996.
U.S. Appl. No. 14/237,042, filed Sep. 16, 2014, now published as US 2015-0030553.
U.S. Appl. No. 14/237,028, filed Jul. 24, 2014, now published as US 2014-0348763.
U.S. Appl. No. 14/237,053, filed Jul. 24, 2014, now published as US 2014-0369943.
U.S. Appl. No. 14/237,027, filed Jul. 16, 2014, now published as US 2014-0329870.
U.S. Appl. No. 14/237,076, filed Jul. 1, 2014, now published as US 2014-0308224.
U.S. Appl. No. 14/358,449, filed May 15, 2014, now published as US 2014-0322151.
U.S. Appl. No. 14/237,032, filed Feb. 4, 2014, now published as US 2016-0000080.
International Preliminary Report on Patentability for PCT/EP2010/002918, dated Dec. 2, 2011.
International Preliminary Report on Patentability for PCT/EP2010/002919, dated Feb. 28, 2012.
International Search Report for PCT/EP2010/002918 dated Jun. 30, 2011.
Bach M. et al. Konservierungsmittel Und Ihre Praktische Anwendung in Kosmetischen Produkten, Sofw-Journal Seifen, Oele, Fette, Wachse, Verlag Fur Chemische Industrie, Angsburg, DE, vol. 116, No. 9, Jun. 13, 1990. pp. 942-7694, XP000134744.
Christian W. Klampfl et al., "Quantitative determination of UV filters in sunscreen lotions using microemulsion electrokinetic chromatography," J. Sep. Sci. Sep. 26, 2003, 1259-1262.
Database CA (Online), Chemical Abstracts Service, Columbus, Ohio (May 12, 1984), Miura Takeshi, Ishida Katsuo; "Rinsing assistants", XP002643079. English abstract of JP 51056809.
Database CA (Online), Chemical Abstracts Service, Columbus, Ohio (May 12, 1984), Miura Takeshi, Ishida Katsuo; "Rinsing assistants", XP002643080. English abstract of JP 51068608.
Database CA (Online), Chemical Abstracts Service, Columbus, Ohio (Sep. 29, 2000), Fukushima Noriko; "Water-soluble rinses for dishwashers", XP002643077.
Database CA (Online), Chemical Abstracts Service, Columbus, Ohio (Sep. 18, 2003), Miura Takeshi, et al.; "Coenzyme Q10-containing emulsions, and manufacture thereof", XP002643081. English abstract of JP 2003238396.
Database CA (Online), Chemical Abstracts Service, Columbus, Ohio (Aug. 14, 2008), Mori Toshiki; "Transparent cleaners comprising nonionic surfactants", XP002643078.
Database GNPD (Online), (Feb. 1999), Mintel; "Verzorgende Shampoo-Lang Harr", XP002662186.
Dubini Francesco et al., "In Vitro Antimycotic Activity and Nail Permeation Models of a Prioctone Olamine (Octopirox) Containing Transungual Water Soluble Technology," Arzneimittel Forschung. Drug Research, ECV Editio Cantor Verlag, vol. 55 No. 8, pp. 478-483, Jan. 1, 2005.
English Abstract for JPH03168075, Jul. 19, 1991.
English Abstract for JPH09291016, Nov. 11, 1997.
English-language abstract of WO 2008/155159 A1.
English-translation of International Preliminary Report on Patentability for PCT/EP2012/003244 dated Feb. 4, 2014.
English-translation of International Preliminary Report on Patentability for PCT/EP2012/003245 dated Feb. 21, 2014.
English-translation of International Preliminary Report on Patentability for PCT/EP2012/003246 dated Feb. 4, 2014.
English-Translation of International Preliminary Report on Patentability for PCT/EP2012/003248 dated Feb. 4, 2014.
English-translation of International Preliminary Report on Patentability for PCT/EP2012/003252 dated Feb. 4, 2014.
English-translation of International Preliminary Report on Patentability for PCT/EP2012/003253 dated Feb. 4, 2014.
F.C. Kull et al., Applied Microbiology 1961, 9, 538.
Giacometti, J. et al., "Process for Preparing Nonionic Surfactant Sorbitan Fatty Acid Esters with and without Previous Sorbitol Cyclization", J. of Agricultural and Food Chemistry, American Chemical Society, vol. 44, Jan. 1, 1996, pp. 3950-3954.
International Search Report for PCT/EP2010/002919 dated Nov. 15, 2011.
International Search Report for PCT/EP2012/003244 dated Oct. 18, 2012.
International Search Report for PCT/EP2012/003245 dated Oct. 5, 2012.
International Search Report for PCT/EP2012/003246 dated Oct. 18, 2012.
International Search Report for PCT/EP2012/003248 dated Oct. 18, 2012

(56) References Cited

OTHER PUBLICATIONS

International Search Report for PCT/EP2012/003249 dated Oct. 5, 2012.
International Search Report for PCT/EP2012/003247 dated Oct. 18, 2012.
International Search Report for PCT/EP2012/003251 dated Oct. 10, 2012.
International Search Report for PCT/EP2012/003252 dated Oct. 8, 2012.
International Search Report for PCT/EP2012/003253 dated Oct. 8, 2012.
International Search Report for PCT/EP2012/004827 dated Jan. 7, 2014.
Translation of International Preliminary Report on Patentability for PCT/EP2012/003249 dated Feb. 4, 2014.
Translation of International Preliminary Report on Patentability for PCT/EP2012/003247 dated Mar. 24, 2014.
Translation of International Preliminary Report on Patentability for PCT/EP2012/003251 dated Feb. 4, 2014.
USPTO Requirement for Restriction/Election for U.S. Appl. No. 14/237,027, dated Jan. 28, 2015.
USPTO Final Rejection for U.S. Appl. No. 13/321,178, dated Dec. 4, 2013.
USPTO Final Rejection for U.S. Appl. No. 13/321,199, dated Mar. 19, 2015.
USPTO Final Rejection for U.S. Appl. No. 13/321,199, dated Dec. 24, 2013.
USPTO Final Rejection for U.S. Appl. No. 14/237,042, dated Jul. 8, 2015.
USPTO Final Rejection for U.S. Appl. No. 14/237,053, dated Sep. 8, 2015.
USPTO Non-Final Rejection for U.S. Appl. No. 13/321,178, dated Apr. 30, 2013.
USPTO Non-Final Rejection for U.S. Appl. No. 13/321,178, dated May 6, 2014.
USPTO Non-Final Rejection for U.S. Appl. No. 13/321,199, dated Apr. 22, 2013.
USPTO Non-Final Rejection for U.S. Appl. No. 13/321,199, dated Aug. 18, 2015.
USPTO Non-Final Rejection for U.S. Appl. No. 13/321,199, dated Sep. 5, 2014.
USPTO Non-Final Rejection for U.S. Appl. No. 14/237,024, dated Mar. 4, 2015.
USPTO Non-Final Rejection for U.S. Appl. No. 14/237,039, dated Aug. 14, 2015.
USPTO Non-Final Rejection for U.S. Appl. No. 14/237,042, dated Dec. 17, 2014.
USPTO Non-Final Rejection for U.S. Appl. No. 14/237,053, dated May 7, 2015.
USPTO Non-Final Rejection for U.S. Appl. No. 14/237,076, dated Sep. 9, 2015.
USPTO Requirement for Restriction/Election for U.S. Appl. No. 13/321,178, dated Jan. 10, 2013.
USPTO Requirement for Restriction/Election for U.S. Appl. No. 13/321,199, dated Nov. 7, 2012.
USPTO Requirement for Restriction/Election for U.S. Appl. No. 14/237,071, dated Jan. 28, 2015.
Frieder W. Lichtenthaler, "Carbohydrates, Chapter 9: Carbohydrates as Organic Raw Materials," Ullmann's Encyclopedia of Industrial Chemistry, vol. 6, pp. 262-273, Jan. 1, 2003.
Seal, Kenneth J. et al., "Benzisothiazolinone and Methylisothiazolinone. New Preservative System," Cosmetic Technology, CEC, vol. 5, No. 1, pp. 47-52, Jan. 1, 2002.
Sorbitan Caprylate—The Preservative Boosting, Multifunctional Ingredient, Frederic Pilz, Cosmetic Science Technology, 2011, pp. 131-134.
A welcome side effect: How Velsan® SC (Sorbitan Caprylate) helps to reduce the concentration of classical preservatives, Fredric Pilz, et al., Household and Personal Care Today, Mar. 2010, pp. 22-24.
Velsan SC: Caprilato de sorbitán—Ingrediente mulfifuncional, conservante, hidrótropo y agente co-emulsionante, Fredric Pilz, et al., NCP 322, Nov.-Dec. 2011, pp. 15-19.
A preservative-free solution, Fredric Pilz, SPC, Oct. 2011.
Presentation by Fredric Pilz, at In-Cosmetics 2010 Paris, Apr. 5, 2010.
Presentation by Fredric Pilz, at SCS Formulate, Nov. 10, 2010.
Presentation by Fredric Pilz, at HPCI Koferenz—Asien, Dec. 17, 2010.
Presentation by Fredric Pilz, at In-Cosmetics 2011 Milano, Mar. 31, 2011.
Presentation by Fredric Pilz, at HPCI Koferenz—Turkey, Jun. 2, 2011.
English Abstract for JP 2008094755, Apr. 24, 2008.
English Abstract for JP 2009078984, Apr. 16, 2009.
English-language Abstract of JP 8173787, Jul. 9, 1996.
English-language Abstract of JP 8187070, Jul. 23, 1996.
Peter Stoss et al., "Regioselektive Acylierung von 1, 4:3, 6-Dianhydro-D-glucit," Synthesis, vol. 1987, No. 02, pp. 174-176, Jan. 1, 1987.
International Search Report for PCT/EP2012/003250 dated Oct. 5, 2012.
Translation of International Preliminary Report on Patentability for PCT/EP2012/003250 dated Feb. 4, 2014.
Translation of International Preliminary Report on Patentability for PCT/EP2012/004827 dated Jan. 7, 2014.
USPTO Notice of Allowance for U.S. Appl. No. 14/237,024, dated Jul. 27, 2015.
USPTO Notice of Allowance for U.S. Appl. No. 14/237,024, dated Nov. 19, 2015.
USPTO Non-Final Rejection for U.S. Appl. No. 14/237,039, dated Oct. 3, 2016.
USPTO Final Rejection for U.S. Appl. No. 14/237,039, dated Feb. 12, 2016.
USPTO Requirement for Restriction/Election for U.S. Appl. No. 14/237,039, dated Apr. 14, 2015.
USPTO Notice of Allowance for U.S. Appl. No. 14/237,039, dated Apr. 18, 2017.
USPTO Non-Final Rejection for U.S. Appl. No. 14/237,042, dated Feb. 25, 2016.
USPTO Notice of Allowance for U.S. Appl. No. 14/237,042, dated Oct. 7, 2016.
USPTO Non-Final Rejection for U.S. Appl. No. 14/237,034, dated Mar. 6, 2015.
USPTO Notice of Allowance for U.S. Appl. No. 14/237,034, dated Aug. 3, 2015.
USPTO Notice of Allowance for U.S. Appl. No. 14/237,034, dated Feb. 10, 2016.
USPTO Non-Final Rejection for U.S. Appl. No. 14/358,449, dated Mar. 3, 2016.
USPTO Final Rejection for U.S. Appl. No. 14/358,449, dated Dec. 15, 2016.
USPTO Non-Final Rejection for U.S. Appl. No. 14/358,449, dated Oct. 17, 2017.

* cited by examiner

COMPOSITION COMPRISING ISOSORBIDE MONOESTERS AND ISOSORBIDE DIESTERS

The present invention relates to compositions comprising isosorbide monoesters and isosorbide diesters and to their use for producing cosmetic, dermatological or pharmaceutical compositions, crop protection formulations, washing or cleaning compositions or paints or coatings.

In industry, there is a large selection of thickeners which can be used to adjust the viscosity of products such as, for example, cosmetic, dermatological or pharmaceutical compositions, crop protection formulations, washing or cleaning compositions, paints or coatings to a desired value.

Correspondingly, also known are numerous preservatives or biocides which can be used to protect such products against microbial attack. For this purpose, use may be made, for example, of preservatives from Annex V of the EU Cosmetics Directive or biocides of the EU Biocides Directive.

However, many thickeners and preservatives have the disadvantage that, frequently, their preparation is expensive and based on synthetic raw materials. In addition, their thickening or preserving action frequently requires improvement, with high use concentrations being required for satisfactory thickening and preservation.

In industry, there is furthermore an increased interest in substances or compositions which already combine the properties mentioned, i.e. which have both advantageous thickener performance and advantageous preservative performance.

Accordingly, it was an object of the present invention to provide substances or compositions which have an advantageous thickening performance and which are furthermore distinguished by the advantage that they are based on renewable raw materials. Advantageously, these substances or compositions should additionally also have advantageous preservative performance.

Surprisingly, it has now been found that this object is achieved by compositions comprising one or more compounds of the formula (I) and one or more compounds of the formula (II)

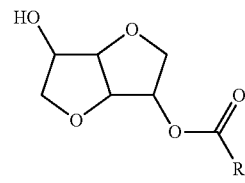
(I)

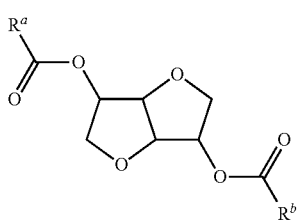
(II)

in which
R, $R^a$ and $R^b$ each independently of one another are straight-chain or branched saturated alkyl groups having 5 to 11, preferably 7 to 9 and particularly preferably 7 carbon atoms or straight-chain or branched mono- or polyunsaturated alkenyl groups having 5 to 11, preferably 7 to 9 and particularly preferably 7 carbon atoms, and where the total amount of the compounds of the formulae (I) and (II), based on the total weight of the composition, is at least 60% by weight.

Thus, the invention provides compositions comprising one or more compounds of the formula (I) and one or more compounds of the formula (II)

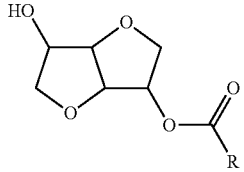
(I)

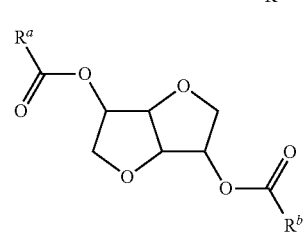
(II)

in which
R, $R^a$ and $R^b$ each independently of one another are straight-chain or branched saturated alkyl groups having 5 to 11, preferably 7 to 9 and particularly preferably 7 carbon atoms or straight-chain or branched mono- or polyunsaturated alkenyl groups having 5 to 11, preferably 7 to 9 and particularly preferably 7 carbon atoms, and where the total amount of the compounds of the formulae (I) and (II), based on the total weight of the composition, is at least 60% by weight.

The compositions according to the invention have both advantageous thickener performance and advantageous preservative performance, preferably against yeasts and fungi and particularly preferably against fungi, and in addition they have the advantage that they are based on renewable raw materials.

The compounds of the formulae (I) and (II) have very good thickener performance and are based on renewable raw materials.

In addition, the compounds of the formula (I) in particular also have very good preservative performance and preferably act as fungicides. In the context of the present invention, this means that the compounds of the formula (I) may preferably act as antimicrobially active compounds against yeasts and fungi. In a particularly preferred embodiment of the invention, the compounds of the formula (I) act as antimicrobially active compounds against fungi.

Compared to the use of organic acids as preservatives, the compounds of the formula (I) additionally have the advantage of being active over a broader pH range. Whereas organic acids frequently only have good activity in the pH range from 3.5 to 6, the compounds of the formula (I) can also be employed advantageously at higher pH.

Compositions which are based at least in part on renewable raw materials and can be used, for example, as preservatives or thickeners are already known.

WO 2010/108738 A2 (Evonik) describes formulations which are used to clean and care for human or animal body parts and comprise sorbitan carboxylic esters, where the carboxylic acid portion of the sorbitan carboxylic ester is derived from a carboxylic acid containing 6 to 10 carbon atoms and the sorbitan carboxylic esters have a hydroxyl number (OH number) of more than 350, and the use of the sorbitan carboxylic esters mentioned as viscosity regulators, care ingredient, foam booster or solubilizer in cleaning or care formulations.

DE 10 2009 022 444 (Clariant) describes liquid compositions comprising sorbitan monocaprylate and antimicrobially active compounds such as, for example, specific organic acids and their salts, specific formeldehyde donors, specific isothiazolinones, specific paraben esters and their salts and specific pyridones and their salts, and also their use for preserving cosmetic, dermatological or pharmaceutical products.

DE 10 2009 022 445 (Clariant) discloses liquid compositions comprising sorbitan monocaprylate and alcohol and their use for preserving cosmetic, dermatological or pharmaceutical products.

JP 8187070 (A) (Lion) discloses a mixture of fatty acid monoesters of $C_8$-$C_{18}$ fatty acids and at least one polyol selected from sorbitol, 1,5-sorbitan, 1,4-sorbitan and isosorbide and fatty acid diesters of these fatty acids and polyols in a weight ratio of monoester:diester of 33:7 to 9:1 as antimicrobially active compound against bacteria for food or beverages.

JP 8173787 (A) (Lion) describes a composition comprising a surfactant comprising a fatty ester of dehydrated sorbitol. The compositions may comprise mono- or diesters of caprylic and/or caprinic acid with a polyol selected from the group consisting of 1,5-sorbitan, 1,4-sorbitan and isosorbide. What is described is in particular the use of the compositions as oil-in-water emulsifier and as cleaner basis.

Compounds of the formulae (I) and (II) can be prepared, for example, by methods familiar to the person skilled in the art. For example, the compounds of the formulae (I) and (II) can be prepared by esterification of isosorbide by customary methods known to the person skilled in the art, with both isosorbide for its part and also the acid component used for esterification once more being commercially available.

Preferably, the weight ratio of the one or more compounds of the formula (I) to the one or more compounds of the formula (II) in the compositions according to the invention is from 5:95 to 95:5.

Preferably, the radicals R, $R^a$ and $R^b$ in the compounds of the formulae (I) and (II) are each independently of one another straight-chain saturated alkyl radicals having 7 to 9 carbon atoms.

Particularly preferably, the radicals R, $R^a$ and $R^b$ in the compounds of the formulae (I) and (II) are straight-chain saturated alkyl radicals having 7 carbon atoms.

In a preferred embodiment of the invention, the compositions according to the invention comprise 0.1 to 1.0, preferably 0.2 to 1.0 and particularly preferably 0.4 to 0.8 parts by weight of the one or more compounds of the formula (II), which is preferably isosorbide dicaprylate, based on 1.0 part by weight of the one or more compounds of the formula (I) and preferably based on 1.0 part by weight of isosorbide monocaprylate.

From among the compositions just mentioned, preference is given to those comprising from 0.05 to 0.7, preferably from 0.1 to 0.6 and particularly preferably from 0.2 to 0.5 part by weight of isosorbide, based on 1.0 part by weight of the one or more compounds of the formula (I) and preferably based on 1.0 part by weight of isosorbide monocaprylate.

In a further preferred embodiment of the invention, the compositions according to the invention comprise from 0.001 to 0.2, preferably from 0.01 to 0.15 and particularly preferably from 0.05 to 0.13 parts by weight of the one or more compounds of the formula (I), which is preferably isosorbide monocaprylate, based on 1.0 part by weight of the one or more compounds of the formula (II) and preferably based on 1.0 part by weight of isosorbide dicaprylate.

In a further preferred embodiment of the invention, the compositions according to the invention comprise, in addition to the one or more compounds of the formula (I) and the one or more compounds of the formula (II), one or more other substances selected from the group consisting of sorbitol, sorbitol esters (sorbitol esters can be mono-, di-, tri-, tetra-, penta- and/or hexaesters), sorbitan, sorbitan esters (sorbitan esters can be mono-, di-, tri- and/or tetraesters), isosorbide and carboxylic acids. "Sorbitan" can be, for example, 1,4- or 1,5-sorbitan. Both the carboxylic acids themselves and the carboxylic acids on which the acid components of the esters mentioned are based correspond to the formula $R^cCOOH$ in which $R^c$ has the meanings given for formulae (I) and (II) for R, $R^a$ and $R^b$ and is preferably a straight-chain saturated alkyl radical having 7 carbon atoms, i.e. the carboxylic acid $R^cCOOH$ is preferably caprylic acid.

In a particularly preferred embodiment of the invention, the hydroxyl value of the mixture of the compounds of the formulae (I) and (II) and additionally the one or more compounds selected from the group consisting of sorbitol, sorbitol esters, sorbitan, sorbitan esters, isosorbide and carboxylic acids in the composition is smaller than or equal to 250, preferably smaller than or equal to 230, particularly preferably smaller than or equal to 210 and especially preferably smaller than or equal to 100.

In a further preferred embodiment of the invention, the compositions according to the invention comprise either no carboxylic acid $R^cCOOH$ or up to 0.1, preferably from 0.0001 to 0.05 and particularly preferably 0.001 to 0.01 parts by weight of carboxylic acid $R^cCOOH$, where $R^c$ has the meaning given for formulae (I) and (II) for R, $R^a$ and $R^b$, and where the carboxylic acid is preferably caprylic acid, based on 1.0 part by weight of the total amount of the one or more compounds of the formula (I) and the one or more compounds of the formula (II) and preferably based on 1.0 part by weight of the total amount of isosorbide monocaprylate and isosorbide dicaprylate.

In a further particularly preferred embodiment of the invention, the compositions according to the invention do not comprise any compounds selected from sorbitol and sorbitol esters. However, if the compositions according to the invention do comprise one or more compounds selected from sorbitol and sorbitol esters (where the carboxylic acid on which the acid component of these esters is based is preferably caprylic acid), these compounds together are preferably present in the compositions according to the invention in an amount smaller than or equal to 5.0% by weight, particularly preferably in an amount smaller than or equal to 3.0% by weight, especially preferably in an amount smaller than or equal to 1.0% by weight and most preferably in an amount smaller than or equal to 0.5% by weight, the stated % by weight in each case being based on the total weight of the finished composition according to the invention.

In a further particularly preferred embodiment of the invention, the compositions according to the invention do not comprise any compounds selected from sorbitan and sorbitan esters. However, if the compositions according to the invention do comprise one or more compounds selected from sorbitan and sorbitan esters (where the carboxylic acid on which the acid component of these esters is based is preferably caprylic acid), these compounds together are preferably present in the compositions according to the invention in an amount smaller than or equal to 20.0% by weight, particularly preferably in an amount smaller than or equal to 10.0% by weight, especially preferably in an amount smaller than or equal to 5.0% by weight and most preferably in an amount smaller than or equal to 1.0% by weight, the stated % by weight in each case being based on the total weight of the finished compositions according to the invention.

In a further particularly preferred embodiment of the invention, the compositions according to the invention each comprise one or more compounds of the formula (I) and (II) and additionally one or more sorbitan esters of sorbitan and carboxylic acids $R^cCOOH$, preferably selected from sorbitan esters from 1,4- and/or 1,5-sorbitan and carboxylic acids $R^cCOOH$ where $R^c$ is a straight-chain or branched saturated alkyl group having 5 to 11, preferably 7 to 9 and particularly preferably 7 carbon atoms or a straight-chain or branched mono- or polyunsaturated alkenyl group having 5 to 11, preferably 7 to 9 and particularly preferably 7 carbon atoms, and where the weight ratio of the compounds of the formulae (I) and (II) together to the one or more sorbitan esters just mentioned is from 70:30 to 100:0, preferably from 80:20 to 100:0, particularly preferably from 90:10 to 100:0 and especially preferably from 95:5 to 100:0. The stated weight ratio of "100:0" means that in this particularly preferred embodiment of the invention, the compositions according to the invention just mentioned do not need to comprise any sorbitan ester.

From among the compositions according to the invention just mentioned, preference is given to those in which the one or more sorbitan esters of sorbitan and carboxylic acids $R^cCOOH$ are selected from sorbitan esters of sorbitan and caprylic acid, preferably selected from sorbitan esters of 1,4- and/or 1,5-sorbitan and caprylic acid and particularly preferably selected from the group consisting of sorbitan monocaprylate and sorbitan dicaprylate.

The hydroxyl value of a substance is to be understood as meaning the amount of KOH in mg equivalent to the amount of acetic acid bound during the acetylation of 1 g of substance.

Suitable determination methods for determining the hydroxyl value are, for example, DGF C-V 17 a (53), Ph. Eur. 2.5.3 Method A and DIN 53240.

In the context of the present invention, the hydroxyl values are determined analogously to DIN 53240-2. Here, the following procedure is adopted: 1 g, accurate to 0.1 mg, of the homogenized sample to be measured is weighed out. 20.00 ml of acetylation mixture (acetylation mixture: 50 ml of acetic anhydride are stirred into 1 liter of pyridine) are added. The sample is dissolved completely in the acetylation mixture, if required with stirring and heating. 5 ml of catalyst solution (catalyst solution: 2 g of 4-dimethylaminopyridine are dissolved in 100 ml of pyridine) are added. The reaction vessel is closed and placed into the water bath, preheated to 55° C., for 10 minutes, with mixing. 10 ml of fully deionized water are then added to the reaction solution, the reaction vessel is closed again and the mixture is once more allowed to react in the water bath with shaking for 10 minutes. The sample is cooled to room temperature (25° C.). 50 ml of 2-propanol and 2 drops of phenolphthalein are then added. This solution is titrated with aqueous sodium hydroxide solution (aqueous sodium hydroxide solution c=0.5 mol/l) (Va). Under identical conditions, but without any sample added, the efficacy of the acetylation mixture is determined (Vb).

From the aqueous sodium hydroxide solution consumed in the determination of the efficacy and the titration of the sample, the hydroxyl value (OHV) is calculated using the following formula:

$$OHV = \frac{(Vb - Va) \cdot c \cdot t \cdot M}{E}$$

OHV=hydroxyl value in mg KOH/g substance
Va=aqueous sodium hydroxide solution consumed in ml during the titration of the sample
Vb=aqueous sodium hydroxide solution consumed in ml during the titration of efficacy
c=molar concentration of the aqueous sodium hydroxide solution in mol/l
t=titer of the aqueous sodium hydroxide solution
M=molar mass of KOH=56.11 g/mol
E=sample weighed out in g
(Vb−Va) is the amount of aqueous sodium hydroxide solution used in ml, which is equivalent to the amount of acetic acid bound during the above-described acetylation of the sample to be measured.

Hereinbelow, the method just described for determining the hydroxyl value is referred to as "method OHV-A".

In an advantageous manner, the compositions according to the invention are suitable for producing cosmetic, dermatological or pharmaceutical compositions, crop protection formulations, washing or cleaning compositions or paints or coatings.

Accordingly, the invention furthermore provides the use of a composition according to the invention for producing cosmetic, dermatological or pharmaceutical compositions, crop protection formulations, washing or cleaning compositions or paints or coatings.

The cosmetic, dermatological or pharmaceutical compositions, the crop protection formulations, the washing or cleaning compositions or the paints or coatings prepared with the aid of the compositions according to the invention comprise the one or more compounds of the formula (I) and the one or more compounds of the formula (II) together, preferably in amounts of from 0.01 to 10.0% by weight, particularly preferably in amounts of from 0.1 to 5.0% by weight and especially preferably in amounts of from 0.2 to 3.0% by weight, in each case based on the total weight of the finished cosmetic, dermatological or pharmaceutical compositions, crop protection formulations, washing or cleaning compositions or paints or coatings.

The cosmetic, dermatological or pharmaceutical compositions, the crop protection formulations, the washing or cleaning compositions or the paints or coatings have viscosities preferably in the range from 50 to 200 000 mPa·s, particularly preferably in the range from 500 to 100 000 mPa·s, especially preferably in the range from 2 000 to 50 000 mPa·s and most preferably in the range from 5 000 to 30 000 mPa·s (20° C., Brookfield RVT, RV spindle set at 20 revolutions per minute).

The cosmetic, dermatological or pharmaceutical compositions are preferably present in the form of fluids, gels, foams, sprays, lotions or creams.

The cosmetic, dermatological or pharmaceutical compositions, the crop protection formulations, the washing or cleaning compositions or the paints or coatings are preferably formulated on an aqueous or aqueous-alcoholic basis or are present as emulsions or dispersions. Particularly preferably, they are present as emulsions, and especially preferably they are present as oil-in-water emulsions.

As further auxiliaries and additives, the cosmetic, dermatological or pharmaceutical compositions, the crop protection formulations, the washing or cleaning compositions or the paints or coatings may comprise all substances customarily used for the application in question, for example oils, waxes, emulsifiers, co-emulsifiers, dispersants, surfactants, defoamers, solubilizers, electrolytes, hydroxy acids, stabilizers, polymers, film formers, further thickeners, gelling agents, superfattening agents, refattening agents, further antimicrobially active compounds, biogenic active compounds, adstringents, active substances, deodorizing compounds, sun protection filters, antioxidants, oxidants, moisturizers, solvents, colorants, pigments, pearlizing agents, fragrances, opacifiers and/or silicones.

The cosmetic, dermatological or pharmaceutical compositions, the crop protection formulations, the washing or cleaning compositions or the paints or coatings have a pH of preferably from 2 to 11, particularly preferably from 4.5 to 8.5 and especially preferably from 5.5 to 6.5.

The examples and applications which follow are intended to illustrate the invention in more detail, without, however, limiting it. All percentages are % by weight, unless explicitly stated otherwise.

EXPERIMENTAL EXAMPLES

A) Preparation of Isosorbide Caprylate 1

In a stirred apparatus with distillation head, 190.0 g (1.3 mol) of isosorbide ("Sorbon" from Ecogreen Oleochemicals) and 187.5 g (1.3 mol) of octanoic acid (caprylic acid) are initially charged at 80° C. together with 0.38 g of aqueous sodium hydroxide solution (18% by weight strength, aqueous) as catalyst. With stirring and under a flow of nitrogen (10-12 liters per hour), the reaction mixture is initially heated to 180° C., where the water of reaction begins to distill off. The reaction is then heated to 190° C. over a period of 1 hour and to 210° C. over a further 2 hours. After 210° C. is reached, the esterification is continued until an acid value of <1 mg KOH/g is reached. This gives 345.7 g of amber isosorbide caprylate (97% of theory). The pH (5% by weight in ethanol/water 1:1) is 5.9. The pH was measured according to DIN EN 1262.

Further analytical characteristics of the isosorbide caprylate 1:
Acid value: 0.9 mg KOH/g, measured according to DIN EN ISO 2114
Hydroxyl value: 206 mg KOH/g, measured analogously to DIN 53240-2 according to method OHV-A
Saponification value: 204 mg KOH/g, measured according to DIN EN ISO 3681

The isosorbide caprylate 1 has the following composition:

| Substance | % by weight |
| --- | --- |
| caprylic acid | 0.4 |
| isosorbide | 18.1 |
| isosorbide monocaprylate | 50.9 |
| isosorbide dicaprylate | 30.6 |

B) Preparation of Isosorbide Dicaprylate

In a stirred 1 liter apparatus under a stream of nitrogen, 219.0 g (1.5 mol) of isosorbide and 461.4 g (3.2 mol) of caprylic acid are heated with stirring and under a stream of nitrogen to 180° C. The reaction mixture was heated at 180° C. until no more water of reaction distilled off (about 28 h). The temperature was then gradually increased to 210° C. (altogether over about 30 h). The reaction has ended when a residual acid value of <2 mg KOH/g is reached. This gives a clear red-brown solution.

Further analytical characteristics of the reaction product:
Acid value: 0.8 mg KOH/g, measured according to DIN EN ISO 2114
Hydroxyl value: 25.2 mg KOH/g, measured analogously to DIN 53240-2 according to method OHV-A
Saponification value: 54.6 mg KOH/g, measured according to DIN EN ISO 3681

For further purification, the product was distilled at a pressure of ≤1 mbar and a bottom temperature of from 210° C. to 240° C. This gives 251.6 g of a clear yellow liquid.

The isosorbide dicaprylate has the following composition:

| Substance | % by weight |
| --- | --- |
| isosorbide monocaprylate | 9.4 |
| isosorbide dicaprylate | 89.6 |
| remainder | 1 |

C) Determination of the Thickener Performance

Using Genapol® LRO (sodium laureth-2 sulfate, 27% by weight in water) and Genagen® KB (cocobetain, 30% by weight in water) and additionally water, a 15% by weight mixture in water comprising the two surfactants in a weight ratio of 8:2 (hereinbelow referred to as "mixture A") is obtained. The thickener performance of isosorbide caprylate 1, isosorbide dicaprylate and isosorbide in mixture A was determined. The results are shown in Table 1.

TABLE 1 measured viscosities

| Substance added to mixture A; amount [% by weight] | Viscosity [mPa · s] |
| --- | --- |
| none | 135 |
| isosorbide caprylate 1 [1% by weight] | 2510 |
| isosorbide dicaprylate [1% by weight] | 2390 |
| isosorbide [1% by weight] | 160 |

As is evident from the results of Table 1, the thickener performance of isosorbide is not worth mentioning, whereas isosorbide caprylate 1 and isosorbide dicaprylate cause significant thickening.

D) Determination of the Antimicrobial Efficacy of Isosorbide Caprylate 1

Below, the antimicrobial efficacy of isosorbide caprylate 1 in butyl polyglycol against bacteria, fungi and yeast is examined. For the tests with bacteria, isosorbide caprylate 1 was diluted with butyl polyglycol and then added to liquid CASO agar (casein-peptone agar) buffered to pH 7 (+/−0.2) in various concentrations (hereinbelow referred to as compositions B1, B2, etc.). For the tests with fungi and yeasts, isosorbide caprylate 1 was diluted with butyl polyglycol and then added to liquid Sabouraud 4% dextrose agar buffered to pH 5.6 (+/−0.2) in various concentrations (hereinbelow referred to as compositions PH1, PH2, etc.). The compositions B1, B2, etc. and PH1, PH2 etc. were each poured into Petri dishes and each inoculated with identical amounts of bacteria, fungi and yeasts. The minimum inhibitory concentration (MIC) is the concentration at which inhibition of the growth of the bacteria, fungi and yeasts in the compositions B1, B2, etc. and PH1, PH2, etc. occurs.

The values determined for the minimum inhibitory concentrations of isosorbide caprylate 1, stated in Table 2 below, have already been corrected for the dilution effect of the butyl polyglycol.

TABLE 2

Minimum inhibitory concentrations (MIC) of isosorbide caprylate 1

| Bacteria (B), fungi (F) or yeasts (Y) examined | MIC of isosorbide caprylate 1 [ppm] |
| --- | --- |
| Staphylococcus aureus (B) | 2500 |
| Pseudomonas aeruginosa (B) | 10000 |
| Escherichia coli (B) | 7500 |
| Enterobacter aerogenes (B) | 10000 |
| Klebsiella pneumoniae (B) | 10000 |
| Proteus vulgaris (B) | 5000 |
| Pseudomonas oleovorans (B) | 10000 |
| Citrobacter freundii (B) | 10000 |
| Candida albicans (H) | 600 |
| Aspergillus brasiliensis (P) | 800 |
| Penicillium minioluteum (P) | 600 |
| Aspergillus terreus (P) | 600 |
| Fusarium solani (P) | 600 |
| Penicillium funicolosium (P) | 400 |

The results listed in Table 2 show that isosorbide caprylate 1 is antimicrobially active, in particular against the yeast *Candida albicans* and the fungi tested.

E) Use Examples

The following formulations are prepared using the composition according to the invention isosorbide caprylate 1.

Formulation Example 1: Revitalizing Moisturizing Cream

| Phase | Ingredient | % by weight |
| --- | --- | --- |
| A | Hostacerin ® SFO | 2.0 |
| | sunflower seed oil sorbitol esters | |
| | Velsan ® CCT | 4.5 |
| | caprylic/capric triglyceride | |
| | Cetiol ® OE | 4.5 |
| | dicaprylyl ether | |
| | Lanette ® 22 | 4.0 |
| | behenyl alcohol | |
| | Lanette ® 18 | 4.0 |
| | stearyl alcohol | |
| | Fucogel ® 1000 | 1.0 |
| | biosaccharide gum-1 | |
| B | Coenzyme ® Q 10 | 0.1 |
| | ubiquinone | |
| C | water | ad 100 |
| | glycerol | 10.0 |
| | Hostaphat ® CK 100 | 0.6 |
| | potassium cetyl phosphate | |
| D | phenoxyethanol | 1.0 |
| | isosorbide caprylate 1 | 1.0 |
| E | NaOH (10% by weight in water) | q.s. |

Preparation:
I The components of A are mixed and the mixture is heated to 80° C.
II The components of C are mixed and the mixture is heated to 80° C.
III B is added to I.
IV II is added to III and the mixture is stirred until it has cooled to room temperature
V D is added to IV
VI The pH is adjusted to 5.5 using E Formulation Example 2

| Phase | Ingredient | % by weight |
| --- | --- | --- |
| A | Hostacerin ® EWO | 16.0 |
| | polyglyceryl 2-sesquiisostearate (and) cera alba (and) carnauba wax (and) ethylhexyl stearate (and) magnesium stearate (and) aluminum stearate | |
| | isopropyl palmitate | 10.0 |
| | avocado oil | 2.0 |
| | Velsan ® CCT | 2.5 |
| | caprylic/capric triglyceride | |
| B | Octopirox ® | 0.05 |
| | piroctone olamine | |
| | propylene glycol | 1.0 |
| C | water | ad 100 |
| | glycerol | 4.0 |
| | magnesium sulfate *7 $H_2O$ | 0.7 |
| | allantoin | 0.5 |
| D | tocopheryl acetate | 0.5 |
| | *Rosmarinus officinalis* (rosemary) leaf oil | 0.1 |
| | urea | 10.0 |
| | isosorbide caprylate 1 | 1.0 |
| | phenoxyethanol | 0.8 |

Preparation:
I The components of A are mixed and the mixture is heated to 80° C.
II The components of B are mixed until all substances have been dissolved (if required with gentle heating)
III II is added to I
IV The components of C are mixed and the mixture is heated to 50° C.
V IV is stirred into I at high speed until the mixture has cooled to 35° C.
VI D is added to V at 35° C.

Formulation Examples 3 and 4: Crop Protection Formulations

| | Formulation No. | |
| --- | --- | --- |
| | 3 | 4 |
| Ingredient | Amount of the respective ingredient [% by weight] | |
| atrazine | 43.6 | 43.6 |
| Dispersogen ® PSL 100 | — | 1.7 |
| Genapol ® LSS | — | 1.6 |
| Dispersogen ® LFS | 2.1 | — |
| propylene glycol | 4.3 | 4.3 |
| Defoamer ® SE 57 | 0.6 | 0.6 |
| Kelzan ® S (2% by weight in water) | 7.3 | 7.3 |
| isosorbide caprylate 1 | 0.3 | 0.2 |
| phenoxyethanol | 1.0 | 1.0 |
| water | ad 100 | ad 100 |

Preparation:

The active ingredient is pre-dispersed with the other ingredients (except for the Kelzan® S solution) and then subjected to fine grinding until the mean particle size is <2 micrometers. The Kelzan® S solution is then stirred in.

Formulation Example 5: Dishwashing Liquids

| Ingredient | % by weight |
|---|---|
| Hostapur ® SAS 60 (alkanesulfonate, 60% by weight in water) | 40.0 |
| Hostapur ® OS liquid (sodium C14-16 alkyl sulfonate, 40% by weight in water) | 11.0 |
| Genaminox ® LA (dimethyllauramine oxide, 30% by weight in water) | 3.0 |
| Genagen ® CAB (cocoamidopropyl betaine, 30% by weight in water) | 3.0 |
| isosorbide caprylate 1 | 0.8 |
| benzyl alcohol | 0.8 |
| water | ad 100 |

Formulation Example 6: Surface Cleaners (All-Purpose Cleaners)

| Ingredient | % by weight |
|---|---|
| Hostapur ® SAS 60 (alkanesulfonate, 60% by weight in water) | 5.0 |
| Genapol ® UD 080 (undecanol + 8 EO) | 2.0 |
| Genaminox ® LA (dimethyllauramine oxide, 30% by weight in water) | 2.0 |
| methylisothiazolinone | 0.01 |
| isosorbide caprylate 1 | 1.0 |
| water | ad 100 |

Preparation of Formulation Examples 5 and 6

Half of the amount of water is initially charged and the components are added by mixing in the same order as listed in the tables given for formulation examples 5 and 6. The remaining amount of water is then added. This gives clear aqueous compositions.

The invention claimed is:

1. A method for controlling a fungus, comprising the step of applying a composition comprising at least one or more compound of the formula (I) and at least one compound of the formula (II)

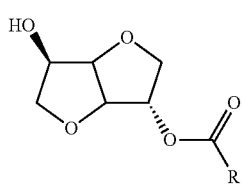

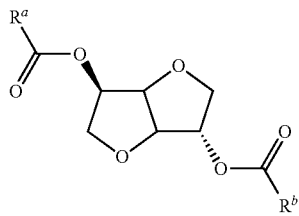

in which

R, $R^a$ and $R^b$ are each independently of one another straight-chain or branched saturated alkyl groups having 5 to 11 carbon atoms or straight-chain or branched mono- or polyunsaturated alkenyl groups having 5 to 11 carbon atoms, wherein the total amount of the compounds of the formulae (I) and (II), based on the total weight of the composition, is at least 60% by weight, where the composition, in addition to the compounds of the formulae (I) and (II), comprises at least one other substance selected from the group consisting of sorbitol, sorbitol esters, sorbitan, sorbitan esters, isosorbide and carboxylic acids and the hydroxyl value of the mixture of the compounds of the formulae (I) and (II) and additionally the one or more compounds selected from the group consisting of sorbitol, sorbitol esters, sorbitan, sorbitan esters, isosorbide and carboxylic acids is smaller than or equal to 250.

2. The method as claimed in claim 1, wherein the weight ratio of the one or more compounds of the formula (I) to the one or more compounds of the formula (II) is from 5:95 to 95:5.

3. The method as claimed in claim 1, wherein the radicals R, $R^a$ and $R^b$ in the formulae (I) and (II) are each independently of one another straight-chain saturated alkyl radicals having 7 to 9 carbon atoms.

4. The method as claimed in claim 3, wherein the radicals R, $R^a$ and $R^b$ in the formulae (I) and (II) are straight-chain saturated alkyl radicals having 7 carbon atoms.

5. The method as claimed in claim 1, wherein the composition comprises from 0.1 to 1.0 part by weight of the at least one compound of the formula (II), based on 1.0 part by weight of the at least one compound of the formula (I).

6. The method as claimed in claim 5, wherein the composition comprises from 0.05 to 0.7 part by weight of isosorbide, based on 1.0 part by weight of the at least one compound of the formula (I).

7. The method as claimed in claim 1, wherein the composition comprises from 0.001 to 0.2 part by weight of the at least one compound of the formula (I), based on 1.0 part by weight of the at least one compound of the formula (II).

8. The method as claimed in claim 1, wherein the composition comprises in each case at least one compound of the formula (I) and (II) and additionally at least one sorbitan ester of sorbitan and a carboxylic acid $R^c$COOH, where $R^c$ is a straight-chain or branched saturated alkyl group having 5 to 11 carbon atoms or a straight-chain or branched mono- or polyunsaturated alkenyl group having 5 to 11 carbon atoms, and where the weight ratio of the compounds of the formulae (I) and (II) together to the at least one sorbitan ester is from 70:30 to 100:0.

9. The method as claimed in claim 8, wherein the at least one sorbitan ester of sorbitan and a carboxylic acid $R^cCOOH$ is selected from the group consisting of sorbitan esters of sorbitan and caprylic acid.

* * * * *